United States Patent [19]

Moore et al.

[11] Patent Number: 5,140,352
[45] Date of Patent: Aug. 18, 1992

[54] CCD CAMERA AND METHOD FOR FUNDUS IMAGING

[75] Inventors: Robert D. Moore, San Mateo; George W. Hopkins, II, Sunnyvale, both of Calif.

[73] Assignee: Occipital, Inc., San Mateo, Calif.

[21] Appl. No.: 606,741

[22] Filed: Oct. 31, 1990

[51] Int. Cl.$^5$ ............................ A61B 3/14; G03B 7/00; G03B 29/00
[52] U.S. Cl. ...................................... 354/62; 351/206; 358/93
[58] Field of Search .......................... 351/206; 354/62; 358/93

[56] References Cited
U.S. PATENT DOCUMENTS
4,773,749 9/1988 Ohtomo et al. .................... 351/206

Primary Examiner—Michael L. Gellner
Attorney, Agent, or Firm—John S. Ferrell

[57] ABSTRACT

A method and apparatus are disclosed for converting the 35 mm image from a conventional fundus camera into a size suitable for recording by a conventional solid state CCD module. The CCD camera connects to the fundus camera using a bayonet attachment. The aerial image created by the fundus camera is received and transmitted through the CCD camera along a folded mirror optical path, and is reduced and aligned for detection by the CCD module. The optical path contains a pair of adjustable mirrors to allow compensation for variations in the focal lengths between various fundus cameras. An articulating mirror may be included to enable the user to pan across the aerial image while recording segmented views for reconstruction by an external computer into a composite, high resolution image.

7 Claims, 8 Drawing Sheets

CCD CAMERA AND METHOD FOR FUNDUS IMAGING

FIELD OF THE INVENTION

This invention relates to an imaging station for ophthamology and more particularly to an optical and electronic interface for fundus cameras that are useful for capturing aerial photographic images of the retina.

BACKGROUND OF THE INVENTION

Fundus cameras are well known in the ophthalmology instrumentation art for use in photographing the optic nerve and other internal features of the eye. A typical fundus camera system, as shown in FIG. 1, includes a fundus camera for making still photographs, a video camera for aligning the fundus camera, a computer system for storing and manipulating video data, and a monitor for displaying the video data transmitted from the video camera.

Interfacing the video system to the fundus camera is traditionally implemented in one of two ways. In the first method, conventional microscope optics are incorporated into the fundus camera and an optical splitter or reflex mirror directs the image between a video camera and the recording film mounted in the fundus camera back. In the second method, a video interface is mounted into the fundus camera back. Both methods have met with less than optimal results. The microscope splitting technique requires the use of relatively expensive optical equipment. The camera back replacement method yields large, relatively unwieldy systems. Both interface techniques tend to disturb the natural balance of the fundus camera and make the system more susceptible to incidental room vibrations. Attempts to stabilize the architectures have resulted in increased cost and weight.

SUMMARY OF THE INVENTION

In accordance with the present invention, an apparatus and method are disclosed for capturing the aerial image produced by a standard fundus camera, for viewing on a video screen and storage within a computer. Specifically, a solid state charge-coupled device (CCD) interface camera attaches to the back of a standard fundus camera and converts the 35 mm aerial image to a size suitable for digital capture by a conventional CCD sensor. In order to overcome the recognized clumsiness of the prior art implementations, a folded mirror scheme is used to fit the 7 to 10 inches of focal length required for image size conversion into a relatively compact and well balanced package.

The CCD camera features a removable bayonet coupling for interfacing the CCD camera to various conventional fundus cameras. Two mirrors along the optical path of the CCD camera are adjustable to allow for compensation among the varying focal lengths of the conventional fundus cameras. A zoom lens allows the operator to take a video image of all of the 22.5 mm (vertical height) of the aerial image, or a reduced portion of the aerial image at higher resolutions. The use of a par focal zoom minimizes refocusing while zooming from larger to smaller fields of view. This capability allows the optical practitioner to examine the optic nerve head, macula, and other areas of interest at extremely high resolution.

Additionally, the disclosed CCD incorporates an articulating mirror along the optic path which can be externally controlled to pan through all or a portion of the aerial image. If a series of images are obtained which slightly overlap, a composite image can be reconstructed using the system computer to orient and match the segments, thereby providing a view having extremely high resolution.

DESCRIPTION OF THE PREFERRED EMBODIMENT

Figure 1A:
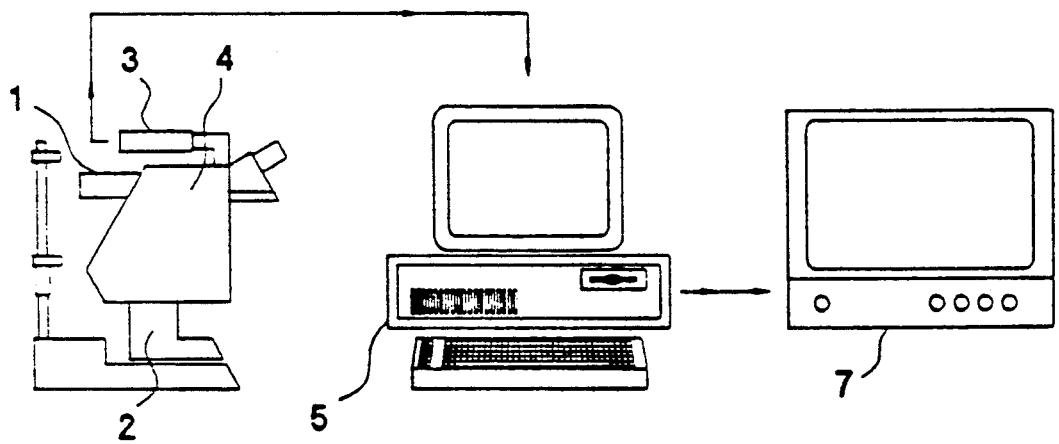
FIG. 1(a) is a schematic diagram showing a typical prior art fundus imaging system.
Figure 1B:
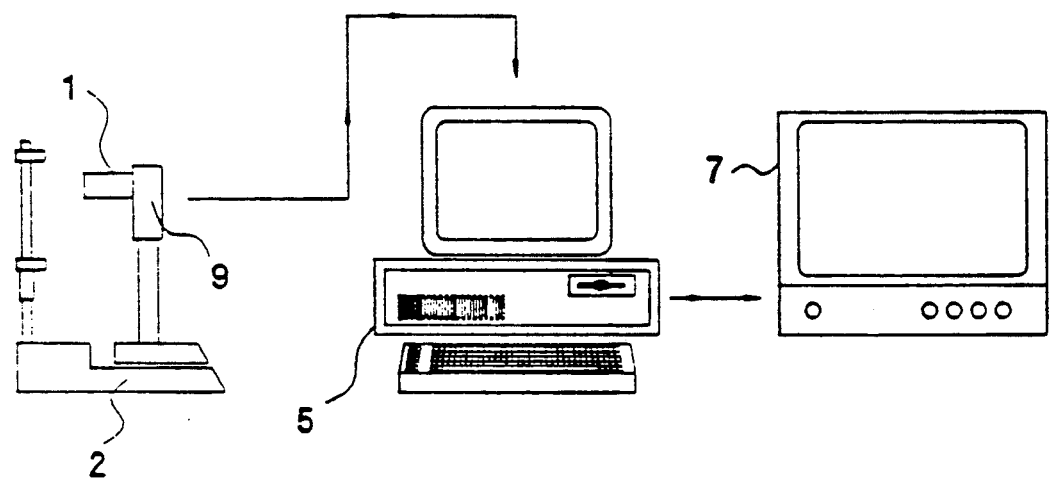
FIG. 1(b) is a schematic diagram showing the preferred embodiment of the disclosed CCD camera.

Referring now to FIG. 1(a), a schematic diagram of a typical prior art system shows a fundus camera 1 mounted on an optical supporting structure 2 and optical interface 4. A video camera 3 permits viewing of the image collected by the fundus camera 1 on the monitor 7. Processing and storage of the images can be effected using a conventional computer 5 connected to the video camera 3. FIG. 1(b) illustrates a similar fundus camera system with the preferred embodiment of the CCD camera 9 replacing the video camera 3 and optical interface 4 of the prior art system in FIG. 1(a).

Figure 2:
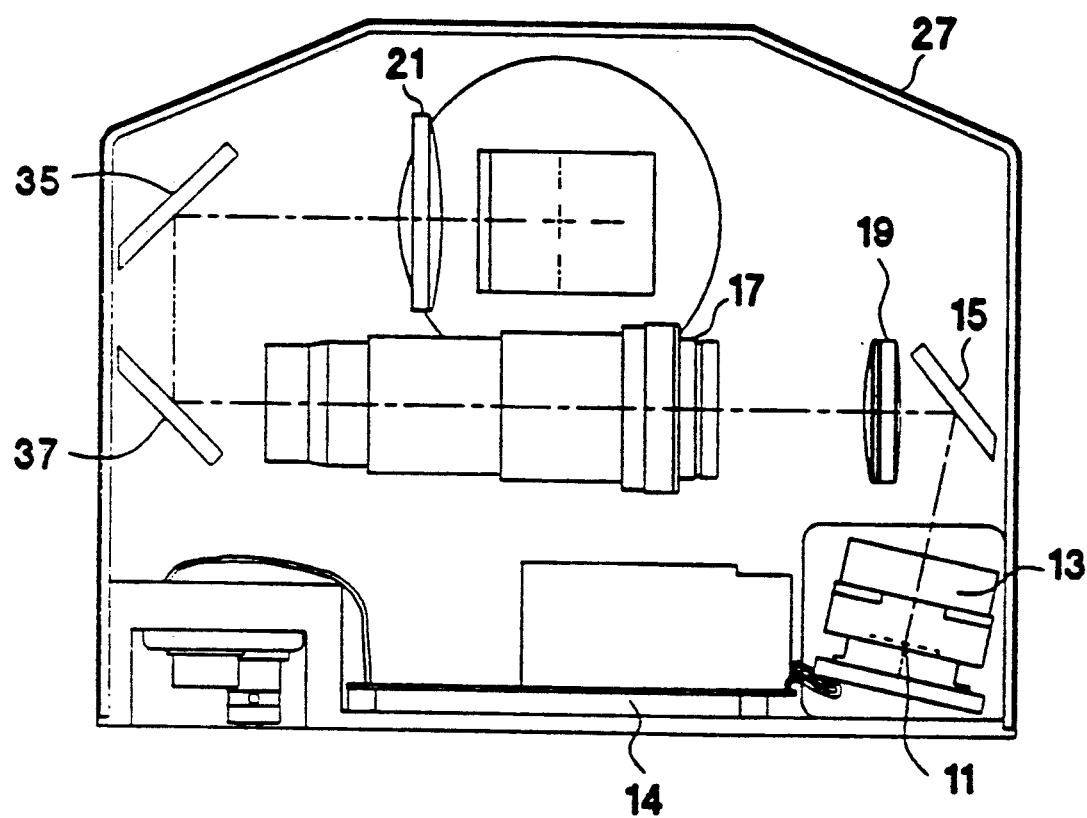
FIG. 2 is a back cross-sectional view of the disclosed CCD camera.
Figure 3:
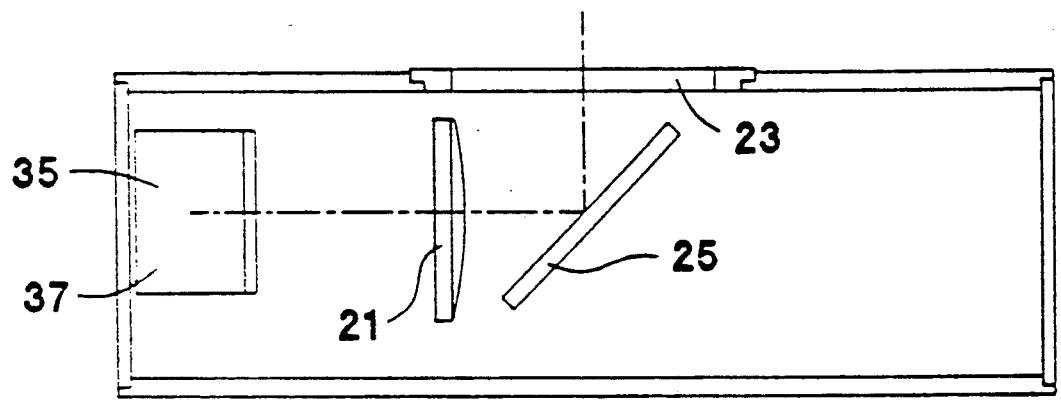
FIG. 3 is a top cross-sectional view of the disclosed CCD camera showing mirror placement.
Figure 4:
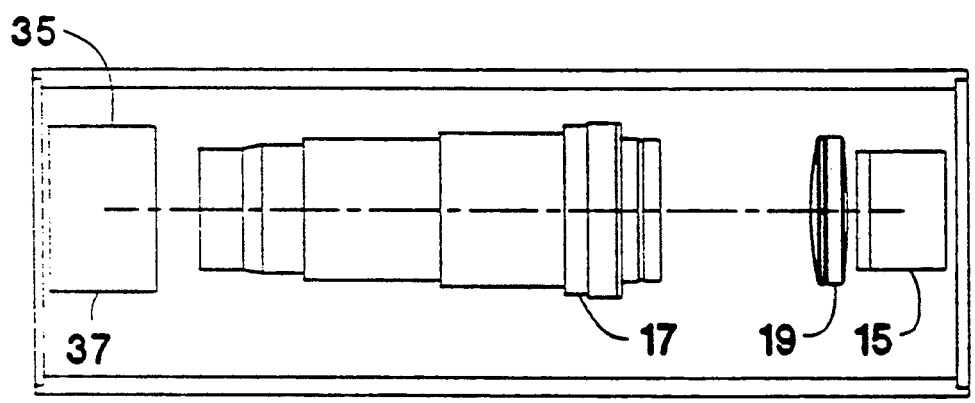
FIG. 4 is a top cross-sectional view of the disclosed CCD camera showing lens placement.
Figure 5:
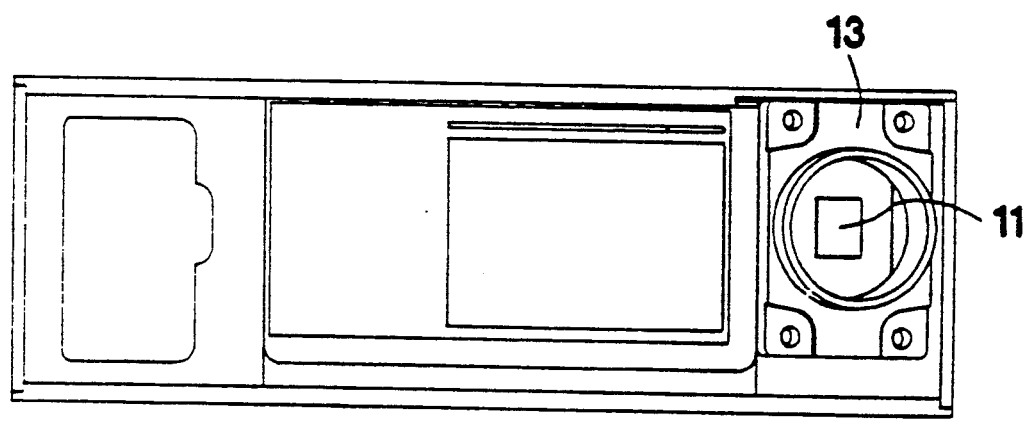
FIG. 5 is a top cross-sectional view of the disclosed CCD camera showing the CCD module placement.
Figure 6:
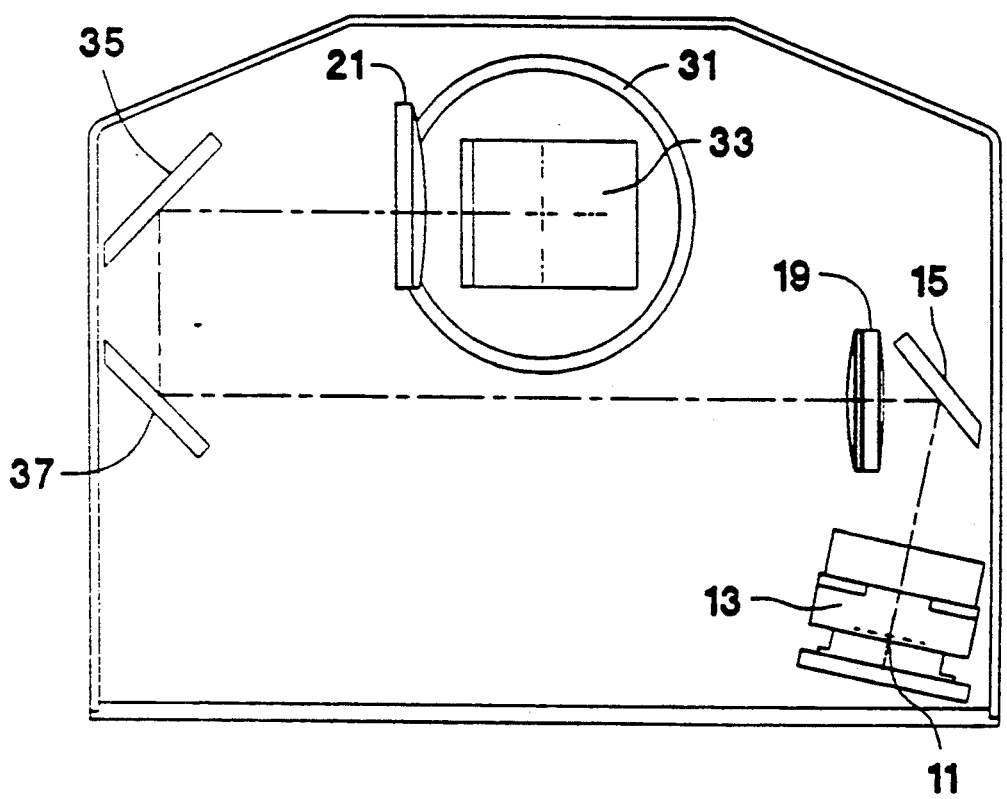
FIG. 6 is a back cross-sectional view of the disclosed CCD camera showing the CCD module and mirrors.
Figure 7:
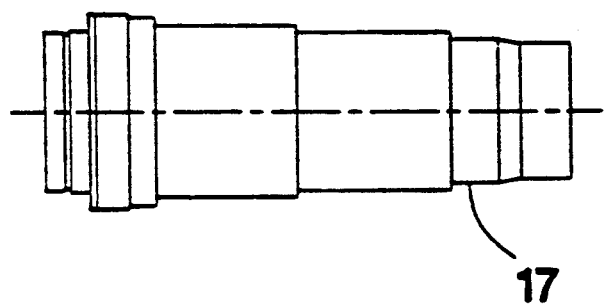
FIG. 7 is a side view of the zoom lens.

Referring now to FIG. 2, a back cross-sectional view of the disclosed CCD camera 9 shows the placement of the major CCD camera 9 components. Referring also to FIG. 6, the CCD camera 9 interfaces to the back-plate of the conventional fundus camera 1 through bayonet coupling 31. This bayonet coupling 31 is removable and may be replaced with optional couplings to accomodate the various conventional fundus cameras 1. The aerial image 33 enters the CCD camera 9 through a window 23 shown most clearly in FIG. 3. This aerial image 33 is in a size format for recording on 35 mm film by the fundus camera 1 and, while traveling through the optical path of the CCD camera 9, will be reduced in size by approximately one-third for recording by the CCD sensor 11.

Upon entering window 23, the aerial image 33 is reflected approximately 90 degrees by a first mirror 25. The reflection is then focussed and aligned by field lens 21. Second and third mirrors 35,37 fold the image through a 180-degree angle and into alignment with zoom lens 17. The second and third mirrors 35,37 are adjustable over a short range to compensate for minor focal length deviations between various brands of fundus cameras 1. Zoom lens 17 is a conventional par focal optic that allows the user to vary the field of view while maintaining a constant focussing of the aerial image 33. This zoom capability allows greatly enhanced resolution of a field within the aerial image 33.

The image exiting the zoom lens 17 is then aligned and compressed by adapter lens 19 and reflected by articulating mirror 15 onto the CCD sensor 11. The articulating mirror 15 allows the user to direct selected portions of the aerial image 33 onto the CCD sensor 11, for example, by panning the articulating mirror 15 across the aerial image 33. In the preferred embodiment the articulating mirror 15 is electronically connected to a joystick or other controller at the computer 5 and remotely actuated to a desired image position by the user. An alternative embodiment may be constructed in which the articulating mirror 15 is controlled by a lever connected to the articulating mirror 15 which passes through the camera case 27. The articulating mirror 15, used in conjunction with the computer 5, enables the construction of a large, high resolution image by taking segmented views using the articulating mirror 15 to pan across the aerial image 33. These segmented views can then be patched together by the computer 5 for use by the ophthalmological practitioner.

The CCD module 13 receives the compressed aerial image 33 from the articulating mirror 15 and aligns the image for recording by the CCD sensor 11. The CCD sensor 11 is of conventional construction and well known in the art. Electronic control of the CCD sensor 11 and coupling of the sensor to the computer 5 and monitor 7 is provided by the electronic interface 14.

We claim:

1. A CCD camera for fundus imaging comprising:
   a bayonet coupling for attaching the CCD camera to a fundus camera;
   a window adjacent to the bayonet for receiving a 35 mm aerial image;
   an optical means located near the window for directing and compressing the aerial image along an optical path; and
   a charge-coupled sensor located in the optical path adjacent to the optical means for collecting and digitizing the compressed aerial image.

2. The CCD camera as in claim 1 wherein said optical means includes a pair of adjustable mirrors for changing the focal length of the optical path.

3. The CCD camera as in claim 1 wherein said optical means includes an articulating mirror for transmitting discrete and selectable portions of the aerial image along the optical path.

4. The CCD camera as in claim 1 wherein said optical means includes a zoom lens for selectively magnifying the aerial image.

5. A method for converting a 35 mm aerial image within an optical path to a size suitable for collection by a charge coupled sensor, wherein the method comprises the steps of:
   receiving the 35 mm aerial image;
   aligning the image along an optical axis;
   compressing the image to a size compatible for detection by the charge-coupled sensor; and
   detection of the compressed image by the charge-coupled device.

6. The method as in claim 5 comprising the additional first step of adjusting the length of the optical path to compensate for focal errors in the 35 mm aerial image.

7. The method as in claim 5 comprising the additional step of magnifying a selected portion of the aligned image prior to detection by the charge-coupled device for increased image resolution.

* * * * *